United States Patent
Prescott (12)

(10) Patent No.: US 6,168,625 B1
(45) Date of Patent: Jan. 2, 2001

(54) ADJUSTABLE LENGTH PROSTHESIS USEFUL FOR OSSICULAR REPLACEMENT AND RECONSTRUCTION

(76) Inventor: Anthony D. Prescott, 8624 N. Lake Cove, Arlington, TN (US) 38002

( * ) Notice: Under 35 U.S.C. 154(b), the term of this patent shall be extended for 0 days.

(21) Appl. No.: 09/201,956

(22) Filed: Dec. 1, 1998

(51) Int. Cl.[7] .................................................. A61F 2/18
(52) U.S. Cl. ............................................................... 623/10
(58) Field of Search ......................................... 623/10, 11

(56) References Cited

U.S. PATENT DOCUMENTS

| D. 286,909 | 11/1986 | Black . | |
|---|---|---|---|
| D. 286,910 | 11/1986 | Black . | |
| 4,281,419 | 8/1981 | Treace . | |
| 4,292,693 | * 10/1981 | Shea et al. ............................. | 623/10 |
| 4,510,627 | 4/1985 | Treace et al. . | |
| 4,597,764 | 7/1986 | Black . | |
| 4,601,723 | 7/1986 | McGrew . | |
| 4,617,024 | * 10/1986 | Broemer et al. ....................... | 623/10 |
| 4,624,672 | 11/1986 | Lenkauskas . | |
| 4,740,209 | * 4/1988 | Gersdorff ............................... | 623/10 |
| 4,871,364 | 10/1989 | Bays et al. . | |
| 5,061,280 | 10/1991 | Prescott . | |
| 5,104,401 | * 4/1992 | Kurz ........................................ | 623/10 |
| 5,180,391 | * 1/1993 | Beoni ..................................... | 623/10 |
| 5,554,188 | * 9/1996 | Prescott ................................. | 623/10 |
| 5,578,086 | * 11/1996 | Prescott ................................. | 623/10 |

* cited by examiner

Primary Examiner—David H. Willse
Assistant Examiner—Suzette J. Jackson
(74) Attorney, Agent, or Firm—Wood, Phillips, VanSanten, Clark & Mortimer

(57) ABSTRACT

An adjustable length prosthesis is used for ossicular replacement or reconstruction. The prosthesis uses a pair of bioactive heads connected by a shaft. The shaft is bendable to accommodate angulation for better anatomical fit. The shaft is flexibly received in the head and trimmable with a scissors or scalpel to simplify length adjustment and prevent chipping and breakage of the bioactive portion. The prosthesis can be used as a total or a partial prosthesis and need not be disassembled and reassembled during the trimming process. The prosthesis can be stabilized on the footplate with a sharpened shaft extension or wire core.

19 Claims, 4 Drawing Sheets

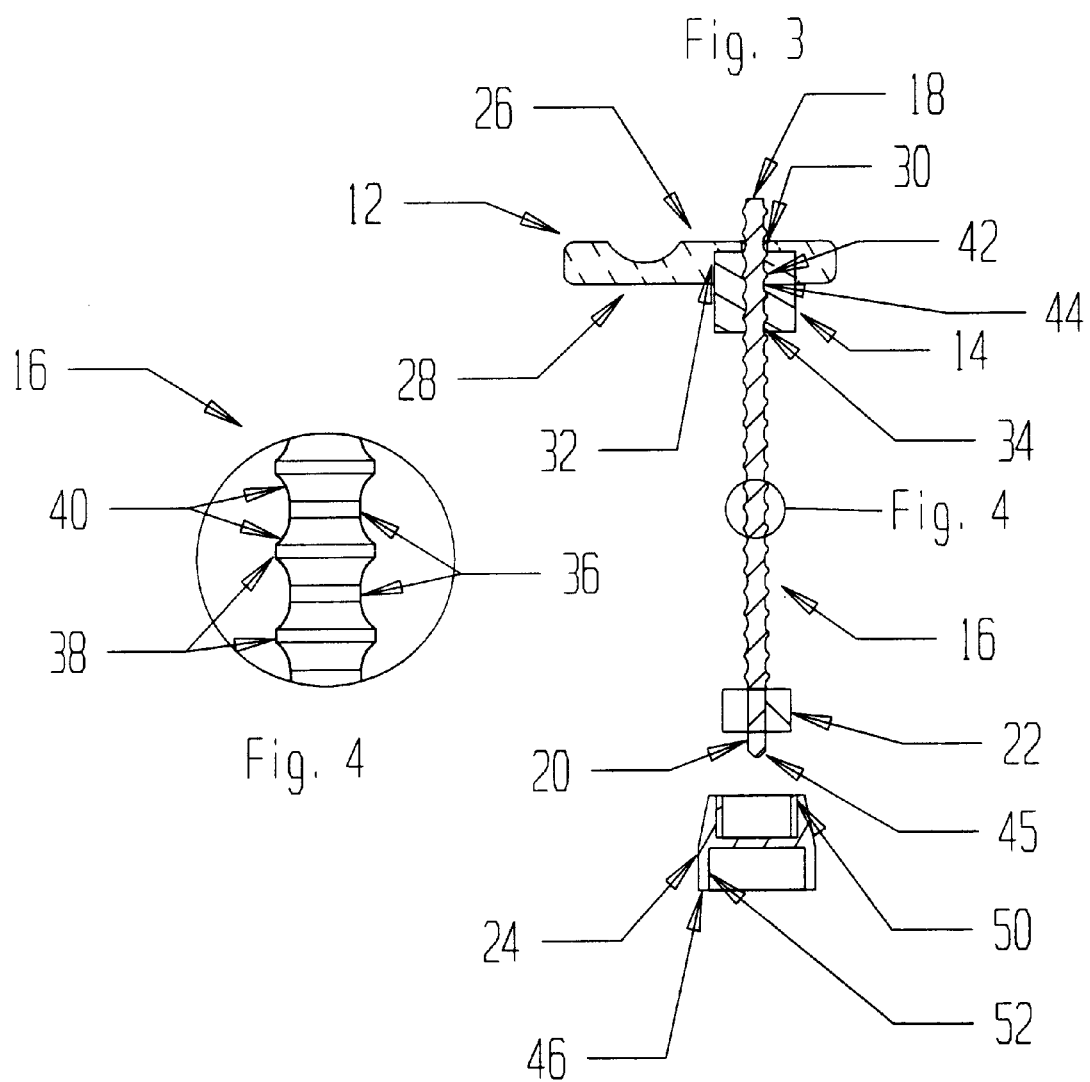

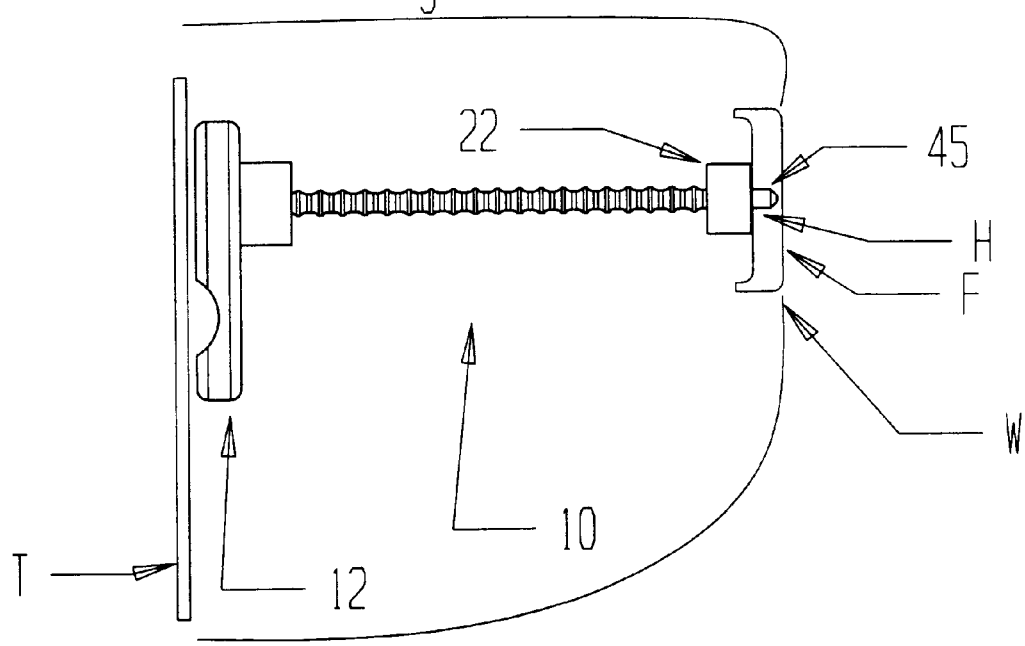
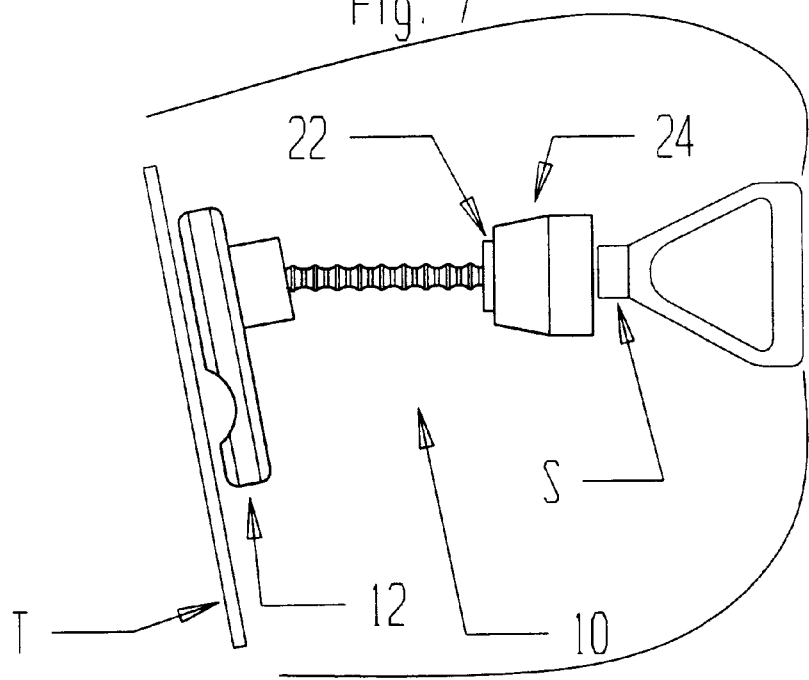

ADJUSTABLE LENGTH PROSTHESIS USEFUL FOR OSSICULAR REPLACEMENT AND RECONSTRUCTION

FIELD OF THE INVENTION

This invention relates to an ossicular prosthesis used for replacement and reconstruction and, more particularly, to an adjustable length ossicular prosthesis.

BACKGROUND OF THE INVENTION

Due to disease, trauma, or congenital malformation, the ossicles of the middle ear are sometime damaged. If this damage results in a discontinuity of bone between the tympanic membrane and the oval window, no sound conducts and hearing loss results. Some or all of these ossicles can be replaced with a small prosthesis. The material of choice for many years has been and, for some surgeons, continues to be the patient's own bone. Usually, the incus body will be harvested and reshaped into a strut that bridges whatever gap exists between the tympanic membrane and the oval window. Although this is an effective method of reconstruction, the time required to harvest and sculpt the incus bone into a usable prosthesis has caused many to search for a suitable synthetic replacement.

Plastic prostheses used for reconstruction of the ossicular chain have been used for some time. A total prosthesis is generally shaped like a nail or tack and replaces all three bones of the middle ear. A partial prosthesis replaces the malleus and the incus ossicles. This prosthesis is similar in shape, but has a hollow cylinder for the reduced portion of the prosthesis. The hollow cylinder fits over the head of the stapes. All plastic prosthesis require that a disc of cartilage be placed between the head of the implant and the tympanic membrane. These discs are harvested during surgery. The disc prevents the implant, in most cases, from eroding the tympanic membrane and becoming dislodged over time "extruding".

Improvements have used movable joints to allow angular adjustment or bendable wire cores. Later, bioactive prostheses were developed. A bioactive material is one which incorporates into the surrounding tissues in the same manner that natural bone would. The bioactive material is usually a calcium phosphate ceramic, such as hydroxylapatite. To trim this type of prosthesis a diamond bur mounted on a surgical drill is used. However, due to the brittle nature of the material, it will sometimes shatter or chip during the trimming process. Bioactive bendable prosthesis use a bioactive ceramic head joined to a bioactive ceramic shaft by a bendable intermediate portion. Such a prosthesis can be angulated for better fit. However, the ceramic shaft must still be trimmed to length.

The present invention is directed to solving one or more of the problems discussed above in a novel and simple manner.

SUMMARY OF THE INVENTION

In accordance with the invention there is disclosed an ossicular prosthesis which is adjustable in length.

Broadly, there is disclosed herein an adjustable length ossicular prosthesis including a head formed of a bioactive or bioinert material for contacting a tympanic membrane when implanted in a human ear. The head includes a through opening. A flexible sleeve is mounted to the head at the through opening. The flexible sleeve includes a through opening coaxial with the head through opening. An elongate shaft has a near end extending through the sleeve through opening and the head through opening. The flexible sleeve through opening is adapted to grip the shaft under static conditions but permit the shaft to move axially to adjust shaft length. Means are associated with a distal end of the shaft for contacting a footplate or stapes when implanted in a human ear.

It is a feature of the invention that the flexible sleeve is formed of a biocompatible material. In one aspect the flexible sleeve is formed of an elastomer such as silicone. Alternatively, the flexible sleeve is formed of a plastic such as Teflon®. The sleeve is held to the head by an adhesive or by mechanical interlock.

It is another feature of the invention that the shaft is formed of a malleable material to produce a bendable shaft. According to one aspect of the invention the shaft is made of titanium.

It is a further feature of the invention that the shaft is defined by alternating enlarged portions and reduced portions and the sleeve expands as the enlarged portions pass through it and contract as the reduced portions pass through. This provides a slip lock mechanism.

It is an additional feature of the invention that the near end of the shaft on the opposite side of the head as the distal end is trimmed.

It is still another feature of the invention that the contacting means comprises a smaller bioactive head for contacting a footplate when implanted in a human ear.

In accordance with another aspect of the invention the contacting means further comprises a cylinder receivable on the smaller head. The cylinder has a counterbore for receiving the head of a stapes when implanted in a human ear.

It is yet another feature of the invention that the shaft extends slightly through the contacting means to form an extended tip to allow surgical fixation of the shaft to a footplate or stapes.

More particularly, an adjustable length prosthesis is used for ossicular replacement or reconstruction. The prosthesis uses a pair of bioactive heads connected by a shaft. The shaft is bendable to accommodate angulation for better anatomical fit. The shaft is flexibly received in the head and trimmable with a scissors or scalpel to simplify length adjustment and prevent chipping and breakage of the bioactive portion. The prosthesis can be used as a total or a partial prosthesis and need not be disassembled and reassembled during the trimming process. The prosthesis can be stabilized on the footplate with a sharpened shaft extension or wire core and can be used to protect the cochlea from pressure trauma.

Further features and advantages of the invention will be readily apparent from the specification and from the drawing.

BRIEF DESCRIPTION OF THE DRAWING

FIG. 3 is a partial sectional view taken along the line 3—3 of FIG. 1;

FIG. 4 is a detailed view of an encircled portion of a shaft of FIG. 3;

FIG. 6 is an elevation view illustrating the prosthesis of FIG. 1 in a human ear when used for total reconstruction; and FIG. 7 is an elevation view illustrating the prosthesis of FIG. 1 in a human ear when used for partial reconstruction.

DETAILED DESCRIPTION OF THE INVENTION

Figure 1:
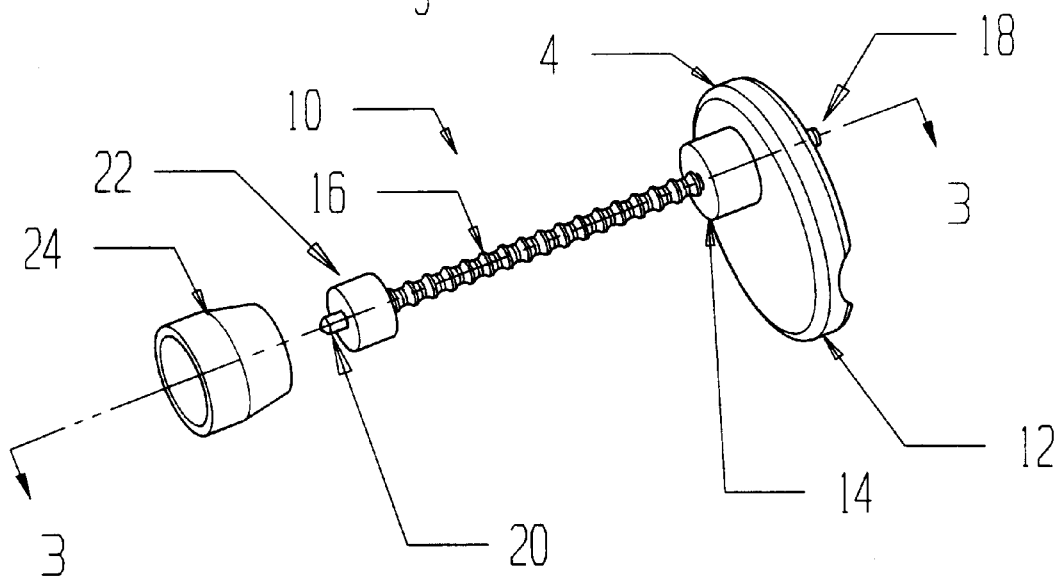
FIG. 1 is a perspective view of an adjustable length ossicular prosthesis according to the invention viewed looking in an outer direction.
Figure 2:
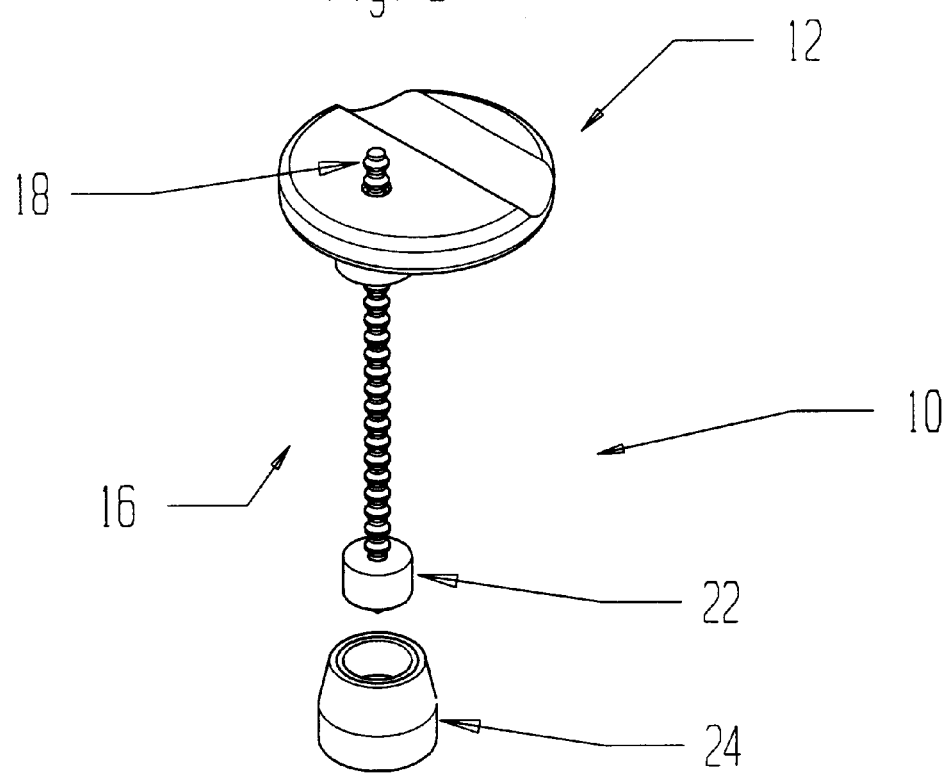
FIG. 2 is a perspective view of the prosthesis of FIG. 1 viewed looking in an inner direction.

Referring to FIGS. 1 and 2, an adjustable length ossicular prosthesis 10 according to the invention is illustrated. In accordance with the invention, the prosthesis 10 can be selectively used for total repair or replacement, as discussed below relative to FIG. 6, or partial repair or replacement, as discussed below relative to FIG. 7.

The prosthesis 10 includes an enlarged head 12 for contacting a tympanic membrane when implanted in a human ear. A flexible sleeve 14 is mounted to the head 12. An elongate shaft 16 has an outer end 18 and a distal or inner end 20. As used herein, the relative terms inner and outer relate to relative position of the prosthesis 10 when placed in a human ear for its intended operation. The shaft 16 extends between the sleeve 14 and a second, smaller head 22. The smaller head 22 is selectively mounted to a cylinder 24 for partial replacement or reconstruction.

The enlarged head 12 is generally circular and has rounded edges. As is apparent to those skilled in the art, the head 12 can be designed using many different shapes and sizes adapted to fit different circumstances. The head 12 comprises a ceramic head. Advantageously, the head 12 is formed of a bioactive material such as hydroxylapatite. Alternatively, it could be formed of a bioglass or even natural bone. The enlarged head 12 is of a shape adapted to contact the tympanic membrane or an ossicle in a human ear. The size of the head 12 is in the range of 2.5 mm to 5.0 mm diameter and 0.5 mm to 2.0 mm thickness.

Referring also to FIG. 3, the head 12 includes an outer surface 26 adapted to contact the tympanic membrane and an inner surface 28. The head 12 includes a relatively small throughbore 30 and a larger coaxial counterbore 32. The throughbore 30 has a diameter slightly larger than a maximum diameter of the shaft 16 to receive the same. The counterbore 32 is formed at the inner surface 28.

The flexible sleeve 14 comprises an expanding cylinder of a size to be received in the head counterbore 32. The sleeve 14 is permanently attached to the head 12. It could be mechanically attached by being directly molded into the head 12. Alternatively, the sleeve 14 could be held in the counterbore 32 using a suitable adhesive or even use a pivoting ball in a socket. The sleeve 14 is formed of a flexible biocompatible material, such as an elastomer or plastic. For example, the sleeve 14 could be formed of an elastomer such as silicone or a plastic such as Teflon®. It. The sleeve 14 is generally cylindrical in shape and includes a through opening 34 which is coaxial with the head through opening 30.

The shaft 16 is formed of a malleable material such as titanium to be bendable. The shaft 16 is adapted to interlock with the sleeve 14. Particularly, as shown in greater detail in FIG. 4, the shaft 16 is defined by a series of alternating enlarged and reduced cross sectional portions. Particularly, the shaft 16 includes reduced portions 36 alternating with enlarged portions 38. The reduced portions 36 are from 0.1 mm to 0.3 mm in diameter and 0.1 mm to 0.3 mm in length. The enlarged portions 38 are from 0.2 mm to 0.5 mm in diameter and from 0.1 mm to 0.3 mm in length. A preferred arrangement is one in which the alternating segments occur in 0.5 mm increments. The enlarged portion 38 and reduced portion 36 are joined by frustoconical portions 40 to aid in length adjustment.

While the shaft 16 is described as being bendable, the prosthesis 10 could be provided with a non-bendable shaft as necessary or desired.

In accordance with the invention, the flexible sleeve 14 is adapted to grip the shaft 16. Particularly, the through opening 34 is adapted to provide a cross-sectional shape generally similar to that of the shaft 16. The through opening 34 includes alternating enlarged portions 42 and reduced portions 44. The opening enlarged portions 42 are of similar size to the shaft enlarged portions 38 and the opening reduced portions 44 are of a similar size to the shaft reduced portions 36. The axial spacing of the enlarged portions 42 and the reduced portions 44 corresponds to the similar spacing of the shaft enlarged portions 38 and reduced portions 36. The flexible sleeve 14 may be molded directly onto the shaft 16 to form the through opening 34.

The smaller head 22 is formed of a bioactive ceramic material, similar to the enlarged head 12. It is rigidly secured to the shaft distal end 20 via a press fit or using an adhesive. The small head 22 is adapted to contact the oval window or footplate in the human ear when the prosthesis 10 is used for total reconstruction. The cross section of the smaller head may be circular, oval or square and is from 0.4 mm to 1.0 mm in diameter. Its length is from 0.5 mm to 2.0 mm.

The shaft distal end 20 extends through the smaller head 22 to form an extended sharpened tip 45. This is done to allow surgical fixation of the shaft 16 to the footplate of the stapes by drilling a hole in the footplate and extending the tip 45 into the hole. As a result, the prosthesis 10 can be stabilized on the footplate with a sharpened shaft extension or wire core.

The cylinder 24 is a bioactive ceramic cylinder, similar to the heads 12 and 22. For example, the cylinder 24 may be formed of hydroxylapatite. The cylinder 24 includes an inner end 46 and a smaller outer end 48. The outer end has a counterbore 50 shown in phantom. The counterbore 50 is of a size and shape corresponding to the smaller head 22 for receiving the same. An enlarged counterbore 52 is positioned at the inner end 46. The cylinder 24 enables the prosthesis 10 to be used for partial reconstruction. Particularly, with the outer counterbore 50 receiving the smaller head 22, the inner end counterbore 52 can engage the head of the stapes. The cylinder outer counterbore 50 may contain a polymeric lining, such as silicone or Teflon® to enhance assembly and hold the cylinder 24 in place during implantation. The cylinder inner counterbore 52 is from 1.0 mm to 2.0 mm in diameter and from 0.5 mm to 2.0 mm in depth.

Figure 5:
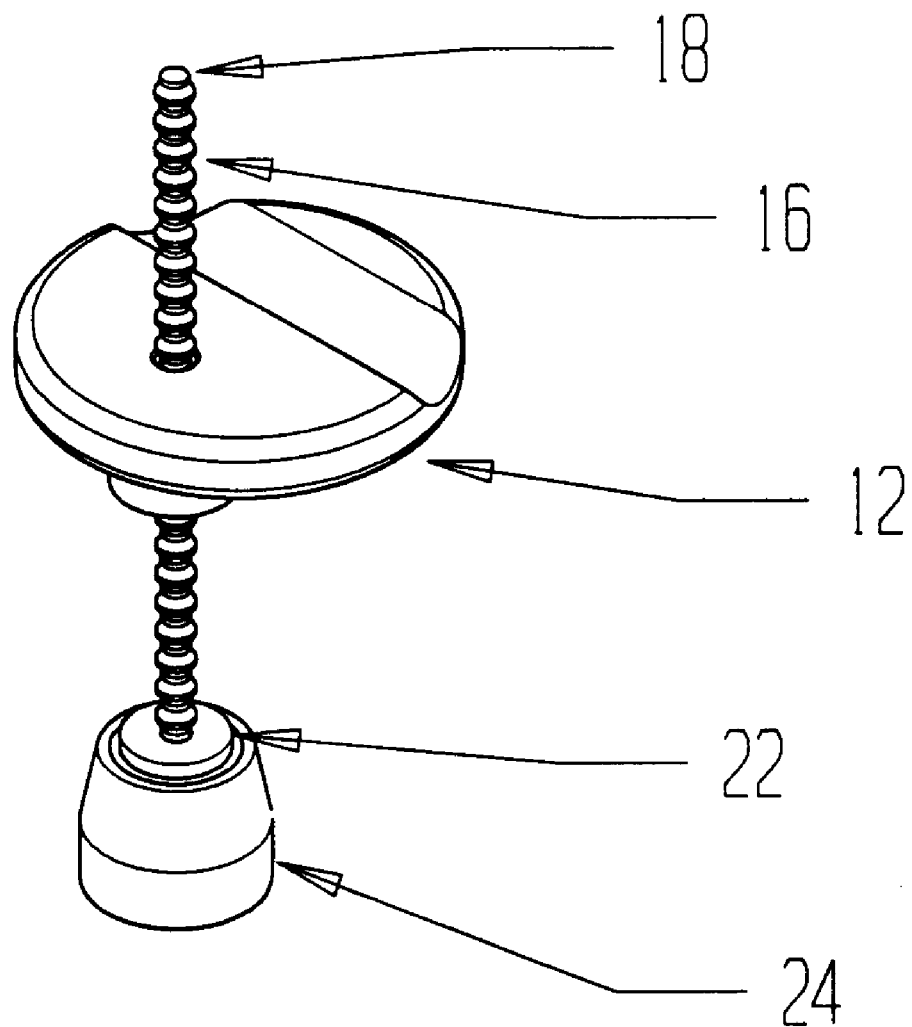
FIG. 5 is a perspective view of the prosthesis of FIG. 1 with its length adjusted for a partial reconstruction.

For ossicular replacement or reconstruction, the surgeon can adjust length in increments determined by the configuration of the shaft 16. Particularly, in the example discussed above, the surgeon can adjust length in 0.5 mm increments defined by spacing between the reduced portions 36. By compressing the enlarged head 12 and smaller head 22, the implant is shortened by forcing the shaft 16 outwardly, as illustrated in FIG. 5. The flexible sleeve 14 expands as the enlarged portions 38 pass through the smaller portions 44 of the through opening 34 and contracted as the smaller portions 36 pass therethrough. By adjusting the mechanical properties of the material of the sleeve 14 or changing the ratio of the enlarged portions 38 and reduced portions 36 of the shaft 16, the tightness of the slip lock may be adjusted. The slip lock should be loose enough to allow easy length adjustment by the surgeon, but tight enough to prevent slippage after implantation. The near end 18 of the shaft that extends outwardly from the head 12, see FIG. 5, can then be cut off by the surgeon prior to implantation.

Although the sleeve 14 and shaft 16 are illustrated having alternating reduced and enlarged cross-sections, such structure is not required in accordance with the teachings of the invention. In fact, one of the two elements could have such a cross-section with the other having a fixed cylindrical cross-section, provided suitable gripping is evident. Moreover, both could have fixed cylindrical cross-section with suitable gripping to prevent slippage. Likewise, the shaft 16 could be formed of a coiled spring or helical thread received in a helical through opening of the sleeve 14. The shaft 16 would then be screwed in or out. This design could be used to protect the cochlea from pressure trauma.

In the illustrated embodiment of the invention, the enlarged head 12, the smaller head 22 and the cylinder 24 are of a bioactive material. Alternatively, these elements could be formed of a bioinert material.

Referring to FIG. 6, the prosthesis 10 is illustrated fitted in a human ear for total reconstruction or replacement. Particularly, the enlarged head 12 contacts the tympanic membrane T. The smaller head 22 contacts the footplate F of the oval window W. The shaft tip 45 is shown, in phantom, in a hole H drilled by the surgeon in the footplate F.

Referring to FIG. 7, the prosthesis 10 is illustrated fitted in a human ear for partial reconstruction or replacement. Particularly, the enlarged head 12 contacts the tympanic membrane T. The smaller head 22 is mounted to the cylinder 24 which receives the head of the stapes S.

Thus, in accordance with the invention there is provided an ossicular prosthesis which provides simple length adjustment and angular orientation.

I claim:

1. An adjustable length ossicular prosthesis comprising:
   a head formed of a bioactive or bioinert material configured for contacting a tympanic membrane when implanted in a human ear, the head including a through opening;
   a flexible sleeve mounted to the head at the through opening, the flexible sleeve including a through opening coaxial with the head through opening;
   an elongate shaft having a near end extending through the sleeve through opening and the head through opening, the flexible sleeve through opening being adapted to grip the shaft under static conditions but permit the shaft to move axially to adjust shaft length; and
   means associated with a distal end of the shaft for contacting a footplate or stapes when implanted in a human ear.

2. The prosthesis of claim 1 wherein the head includes a counterbore receiving the flexible sleeve.

3. The prosthesis of claim 2 wherein the counterbore is coaxial with the head through opening.

4. The prosthesis of claim 2 wherein the sleeve is secured in the counterbore with an adhesive.

5. The prosthesis of claim 1 wherein the sleeve comprises an elastomer sleeve.

6. The prosthesis of claim 1 wherein the sleeve comprises a silicone sleeve.

7. The prosthesis of claim 1 wherein the sleeve comprises a plastic sleeve.

8. The prosthesis of claim 1 wherein the sleeve comprises a Teflon sleeve.

9. The prosthesis of claim 1 wherein the shaft is defined by alternating reduced cross section portions and enlarged cross section portions.

10. The prosthesis of claim 1 wherein the shaft comprises a bendable shaft.

11. The prosthesis of claim 1 wherein the shaft comprises a titanium shaft.

12. The prosthesis of claim 1 wherein the sleeve through opening is defined by alternating reduced portions and enlarged portions.

13. The prosthesis of claim 12 wherein the shaft is defined by alternating reduced cross section portions and enlarged cross section portions to be received in the respective through opening reduced and enlarged portions to provide a slip lock.

14. The prosthesis of claim 1 wherein the contacting means comprises a smaller head of bioactive or bioinert material for contacting a footplate when implanted in a human ear.

15. The prosthesis of claim 14 wherein the contacting means comprises a cylinder mounted to the smaller head, the cylinder having a counterbore receiving a head of a stapes when implanted in a human ear.

16. The prosthesis of claim 15 wherein the cylinder is of bioactive or bioinert material.

17. The prosthesis of claim 1 wherein the contacting means comprises a cylinder mounted to the shaft, the cylinder having a counterbore receiving a head of a stapes when implanted in a human ear.

18. The prosthesis of claim 16 wherein the cylinder is of bioactive or bioinert material.

19. The prosthesis of claim 1 wherein a portion of the shaft extends beyond the contacting means to be received in a hole formed in a footplate when implanted in the human ear to stabilize the prosthesis.

* * * * *